US011419922B2

(12) United States Patent
Finzi et al.

(10) Patent No.: US 11,419,922 B2
(45) Date of Patent: Aug. 23, 2022

(54) TREATMENT OF POST-TRAUMATIC STRESS DISORDER USING BOTULINUM TOXIN A (71) Applicants: Eric Finzi, Bethesda, MD (US); Norman E. Rosenthal, Rockville, MD (US)

(72) Inventors: Eric Finzi, Bethesda, MD (US); Norman E. Rosenthal, Rockville, MD (US)

(*) Notice: Subject to any disclaimer, the term of this patent is extended or adjusted under 35 U.S.C. 154(b) by 683 days.

(21) Appl. No.: 14/443,359

(22) PCT Filed: Nov. 15, 2013

(86) PCT No.: PCT/US2013/070408
§ 371 (c)(1),
(2) Date: May 15, 2015

(87) PCT Pub. No.: WO2014/078724
PCT Pub. Date: May 22, 2014

(65) Prior Publication Data
US 2016/0256531 A1 Sep. 8, 2016

Related U.S. Application Data (60) Provisional application No. 61/727,595, filed on Nov. 16, 2012.

(51) Int. Cl.
A61K 38/48 (2006.01)
A61K 45/06 (2006.01)
A61K 9/00 (2006.01)
G09B 7/06 (2006.01)

(52) U.S. Cl.
CPC ........ A61K 38/4893 (2013.01); A61K 9/0019 (2013.01); A61K 45/06 (2013.01); G09B 7/06 (2013.01); C12Y 304/24069 (2013.01)

(58) Field of Classification Search
CPC ................ A61K 38/4893; A61K 45/06; C12Y 304/24069
See application file for complete search history.

(56) References Cited

U.S. PATENT DOCUMENTS

| | | | |
|---|---|---|---|
| 5,714,468 A | 2/1998 | Binder | |
| 6,358,917 B1 | 3/2002 | Carruthers et al. | |
| 7,393,537 B2 | 7/2008 | Ackerman | |
| 7,758,872 B1 | 7/2010 | Finzi | |
| 7,811,587 B2 | 10/2010 | Donavan | |
| 7,824,694 B2 | 11/2010 | Finzi | |
| 7,846,457 B2 | 12/2010 | Steinsapir | |
| 8,414,902 B2 | 4/2013 | Finzi | |
| 8,501,195 B2 | 8/2013 | Turkel et al. | |
| 8,609,112 B2 | 12/2013 | Blumenfeld et al. | |
| 8,609,113 B2 | 12/2013 | Blumenfeld et al. | |
| 8,617,572 B2 | 12/2013 | Blumenfeld | |
| 8,734,810 B2 | 5/2014 | Blumenfeld | |
| 8,747,865 B2 | 6/2014 | Ackerman | |
| 8,889,151 B2 | 11/2014 | Turkel | |
| 8,926,991 B2 | 1/2015 | Borodic | |
| 8,940,308 B2 | 1/2015 | Turkel et al. | |
| 9,060,964 B2 | 6/2015 | Finzi | |
| 9,078,892 B2 | 7/2015 | Turkel | |
| 9,078,893 B2 | 7/2015 | Turkel | |
| 9,254,314 B2 | 2/2016 | Finzi | |
| 9,533,029 B2 | 1/2017 | Finzi | |
| 2006/0083758 A1 | 4/2006 | Dadas | |
| 2007/0009555 A1* | 1/2007 | Borodic | A61K 38/4893 424/239.1 |
| 2009/0324647 A1 | 12/2009 | Borodic | |
| 2010/0189655 A1 | 7/2010 | Turkel et al. | |
| 2010/0249036 A1 | 9/2010 | Finzi | |
| 2011/0200639 A1 | 8/2011 | Blumenfeld | |
| 2011/0218215 A1 | 9/2011 | Holly | |
| 2012/0021991 A1 | 1/2012 | Ackerman | |
| 2013/0142776 A1 | 6/2013 | Blumenfeld | |
| 2013/0142777 A1 | 6/2013 | Blumenfeld | |
| 2013/0150307 A1 | 6/2013 | Turkel et al. | |
| 2013/0189307 A1 | 7/2013 | Finzi | |
| 2013/0224180 A1 | 8/2013 | Turkel et al. | |
| 2013/0330321 A1 | 12/2013 | Turkel et al. | |
| 2014/0099298 A1 | 4/2014 | Blumenfeld | |

(Continued)

FOREIGN PATENT DOCUMENTS

| | | |
|---|---|---|
| EP | 2394645 | 12/2011 |
| WO | WO 2006/13 8127 | 12/2006 |

(Continued)

OTHER PUBLICATIONS

Forbes et al. "The validity of the PTSD checklist as a measure of symptomatic change in combat-related PTSD" Behaviour Research and Therapy 39 (2001) 977-986.*

(Continued)

Primary Examiner — Robert J Yamasaki
(74) Attorney, Agent, or Firm — Klarquist Sparkman, LLP (57) ABSTRACT Methods are disclosed for treating post traumatic stress disorder (PTSD) in a subject. The methods include administering a therapeutically effective amount of a neurotoxin to a corrugator supercilii and/or a procerus muscle of the subject to cause paralysis of the corrugator supercilii and/or a procerus muscle in the subject, thereby treating PTSD. The neurotoxin can be Botulinum toxin A, such as at a dose of about 20 to about 50 units of Botulinum toxin A.

20 Claims, 3 Drawing Sheets (56) References Cited

U.S. PATENT DOCUMENTS

| | | | |
|---|---|---|---|
| 2014/0205590 | A1 | 7/2014 | Blumenfeld |
| 2015/0132282 | A1 | 5/2015 | Finzi et al. |
| 2015/0258183 | A1 | 9/2015 | Borodic |
| 2015/0290302 | A1 | 10/2015 | Finzi |
| 2016/0114015 | A1 | 4/2016 | Finzi |
| 2016/0166658 | A1 | 6/2016 | Finzi |
| 2017/0014493 | A1 | 1/2017 | Finzi |
| 2017/0258879 | A1 | 9/2017 | Finzi et al. |

FOREIGN PATENT DOCUMENTS

| | | | |
|---|---|---|---|
| WO | WO 2007/044809 | | 4/2007 |
| WO | WO 2014/035966 | | 3/2014 |
| WO | WO 2012/174123 | A1 | 12/2014 |
| WO | WO 2015/011447 | | 1/2015 |
| WO | WO 2015/073441 | | 5/2015 |

OTHER PUBLICATIONS

Lippert-Grüner "Botulinum toxin in the treatment of post-traumatic headache—case study," *Neurologio i Neurochirurgio Polska* 46(6): 591-594 (Jan. 1, 2012).

International Search Report from the parent PCT Application No. PCT/US2013/070408, 3 pages (dated Mar. 18, 2014).

Written Opinion from the parent PCT Application No. PCT/US2013/070408, 5 pages (dated Mar. 18, 2014).

Adelmann et al., "Facial efference and the experience of emotion," *Ann. Rev. Psychol.* 40:249-280 (1989).

Brenner et al., "Acute anxiety and depression induced by loss of sensation and muscle control after botulinum toxin A injection," *South Med J* 92(7): 738 (1999).

Cardiff University News and Views, "Treating laughter lines leaves patients feeling more depressed," (Apr. 11, 2013), available on line at http://www.cardiff.ac.uk/news/view/45697-treating-laughter-lines-leaves-patients-feeling-more-depressed.

Cassels, "More evidence botox works for depression," *Medscape Medical News* (Jun. 2014), available on line at http://www.webmd.com/depression/news/20140619/botox-depression.

Cohen, "Rational drug use in the treatment of depression," *Pharmacotherapy* 17(1):45-61 (Jan.-Feb. 1997) (Abstract only).

Cole, *About Face*, The MIT Press, Massachusetts Institute of Technology, Cambridge, MA (1998)(Abtract).

Darwin, The expression of the emotions in man and animals, University of Chicago Press, Chicago, IL, 1965, as shown at: http://rcin.org.pl/Content/1674/WA488_4313_185_Darwin-The-expresssion.pdf, (Accessed May 11, 2017).

Finzi and Rosenthal, "Neuropsychopharmacology," *51st Annual Meeting of the American College of Neuropsychopharmacology*, ACNP 2012. Hollywood, FL, United States 38(Supp.l): S316 (Dec. 6, 2012)(Abstract).

Finzi and Rosenthal, "Treatment of depression with onabotulinumtoxinA: A randomized, double-blind, placebo controlled trial," *Journal of Psychiatric Research* 52: 1-6 (2014).

Finzi and Wasserman, "Treatment of depression with botulinum toxin A: A case series," *Dermatologic Surgery* 32(5): 645-650 (2006).

Fried et al., "The botulinum toxin experience results of a patient self-report questionnaire," Journal of Clinical and Aesthetic Dermatology 2(11): 37-40 (Nov. 2009).

Gudex et al., "Effect of dystonia and botulinum toxin treatment on health-related quality of life," *Mov. Disord* 13(6): 941-946 (1998) (Abstract only).

Heckmann et al., "Pharmacologic denervation of frown muscles enhances baseline expression of happiness and decreases baseline expression of anger, sadness, and fear," *J. Am. Acad. Dermatol.* 49(2): 213-216 (2003) (Abstract only).

Jahanshahi et al., "Psychological functioning before and after treatment of torticollis with botulinum toxin," *Journal of Neurology, Neurosurgery and Psychiatry* 55: 229-231 (1992).

Kim et al., "Botulinum toxin-induced facial muscle paralysis affects amygdala responses to the perception of emotional expressions: preliminary findings from an A-B-A design," *Biology of Mood & Anxiety Disorders* 4: 11 (8 pages) (2014).

Muller et al., "The impact of blepharospasm and cervical dystonia on health-related quality of life and depression," *J. Neurol.* 249(7): 842-846 (2002) (Abstract).

Murry et al., "Spasmatic dysphomia, emotional status and botulinum toxin treatment," *Arch Otolaryngol Head Neck Surg.* 120: 310-316 (Mar. 1994)(Abstract).

Wagstaff et al., "Paroxetine: an update of its use in psychiatric disorders in adults," *Drugs* 62(4): 655-703 (2002) (Abstract only).

Wollmer et al., "Facing depression with botulinum toxin: A randomized controlled trial," *Journal of Psychiatric Research* 46(5): 574-581 (May 2012).

Friedman et al., "Classification of trauma and stressor-related disorders in DSM-5," *Depression and Anxiety* 28: 737-749 (2011).

Friedman, "Toward rational pharmacotherapy for posttraumatic stress disorder: Reprise," *American Journal of Psychiatry* 170(9): 944-946 (Sep. 2013).

Liu-Barbaro and Stein, "Psychopharmacologic treatment of dissociative fugue and PTSD in an Ethiopian refugee," *Journal of Psychiatry* 76(7): 958 (epub Jun. 9, 2015).

Martenyi et al., "Failed efficacy of fluoxetine in the treatment of posttraumatic stress disorder, Results of a fixed-dose, placebo-controlled study" *Journal of Clinical Psychopharmacology* 27(2): 166-170 (Apr. 2007).

Stahl., "Mechanism of action of serotonin selective reuptake inhibitors; Serotonin receptors and pathways mediate therapeutic effects and side effects," *Journal of Affective Disorders* 51: 215-235 (1998).

Aupperle et al., "Dorsolateral prefrontal cortex activation during emotional anticipation and neuropsychological performance in post-traumatic stress disorder," *Archives of General Psychiatry* 69:360-371 (2012).

Boldrini et al., "Hippocampal granule neuron number and dentate gyrus volume in antidepressant-treated and untreated major depression," *Neuropsychopharmacology* 38:1068-1077 (2013).

Bremner et al., "Hippocampal volume reduction in major depression," *Am J Psychiatry* 157:115-118 (2000).

Bremner et al., "Reduced volume of orbitofrontal cortex in major depression," *Biol Psychiatry* 51:273-279 (2002).

Cao et al., "Disrupted resting-state functional connectivity of the hippocampus in medication-naive patients with major depressive disorder," *J Affect Disord.* 141:194-203 (2012).

Cole et al., "Hippocampal atrophy in first episode depression: a meta-analysis of magnetic resonance imaging studies," *J Affect Disord.* 134:483-487 (2011).

Delaveau et al., "Brain effects of antidepressants in major depression: a meta-analysis of emotional processing studies," *J Affect Disord.* 130:66-74 (2011).

Drevets "Functional anatomical abnormalities in limbic and prefrontal cortical structures in major depression," *Prog Brain Res.* 126:413-431 (2000).

Frodl et al., "Association of the brain-derived neurotrophic factor Val66Met polymorphism with reduced hippocampal volumes in major depression," *Arch Gen Psychiatry* 64:410-416 (2007).

Fu et al., "Predictive neural biomarkers of clinical response in depression: a meta-analysis of functional and structural neuroimaging studies of pharmacological and psychological therapies," *Neurobiol Dis.* 52:75-83 (2013).

Jaworska et al., "A review of fMRI studies during visual emotive processing in major depressive disorder," *World J Biol Psychiatry* 16:448-471 (2015).

Lanius et al., "Neural correlates of trauma script-imagery in post-traumatic stress disorder with and without comorbid major depression: A functional MRI investigation," *Psychiatry Research-Neuroimaging* 155:45-56 (2007).

Levy et al., "Neurotrophic factors and neuroplasticity pathways in the pathophysiology and treatment of depression," *Psychopharmacology* 235: 2195 (2018).

Liberzon and Abelson "Context Processing and the Neurobiology of Post-Traumatic Stress Disorder," *Neuron* 92(1):14-30 (Oct. 5, 2016).

(56) References Cited

OTHER PUBLICATIONS

Lindauer et al., "Effects of psychotherapy on regional cerebral blood flow during trauma imagery in patients with post-traumatic stress disorder: a randomized clinical trial," *Psychological Medicine* 38:543-554 (2008).

Nordanskog et al., "Hippocampal volume in relation to clinical and cognitive outcome after electroconvulsive therapy in depression," *Acta Psychiatr Scand.* 129:303-311 (2014).

Rougemont-Bucking et al., "Altered processing of contextual information during fear extinction in PTSD: an fMRI study," *CNS Neuroscience & Therapeutics* 17:227-236 (2011).

Russo and Nestler "The brain reward circuitry in mood disorders," *Nat Rev Neurosci.* 14:609-662 (2013).

Seeley et al., "Dissociable intrinsic connectivity networks for salience processing and executive control," *J Neurosci.* 27:2349-2356 (2007).

Sheline et al., "The default mode network and self-referential processes in depression," *Proc Natl Acad Sci.* 106:1942-1947 (2009).

\* cited by examiner

TREATMENT OF POST-TRAUMATIC STRESS DISORDER USING BOTULINUM TOXIN A

CROSS REFERENCE TO RELATED APPLICATIONS

This is the U.S. National Stage of PCT Application No. PCT/US2013/070408 filed Nov. 15, 2013, which was published in English under PCT Article 21(2), which claims the benefit of U.S. Provisional Application No. 61/727,595, filed Nov. 16, 2012, which is incorporated herein by reference.

FIELD

This disclosure relates to the field of psychiatric disorders and in particular, to methods for treating post-traumatic stress syndrome (PTSD) that utilize a neurotoxin such as a botulinum toxin.

BACKGROUND

Post-traumatic stress disorder (PTSD) is a severe psychological disorder that can develop after exposure to an event that results in psychological trauma. This event can involve the threat of death to the individual, but it can also involve a threat to the physical, sexual, or psychological integrity of the patient. Generally, PTSD overwhelms an individual's ability to function in normal day to day activities. Diagnostic symptoms for PTSD include re-experiencing the original trauma(s) through flashbacks or nightmares, avoidance of stimuli associated with the trauma, and increased arousal. The symptoms can also include difficulty falling or staying asleep, anger, and hypervigilance. Formal diagnostic criteria in both the American Psychiatric Association's Diagnostic and Statistical Manual, Fourth Edition (DSM-IV); American Psychiatric Publishing, Inc., Washington D.C., 2000, and the International Statistical Classification of Disease and Related Health Problems (ICD-10) require that the symptoms last more than one month and cause significant impairment in social, occupational, or other important areas of functioning. Although most people (50-90%) encounter trauma over a lifetime, only about 8% develop full PTSD. Vulnerability to PTSD is believed to stem from an interaction of biological diathesis, early childhood developmental experiences, and trauma severity, After diagnosis of PTSD, modest benefits have been seen from early access to cognitive behavioral therapy, as well as from some medications such as propranolol. Many forms of psychotherapy have been advocated for trauma-related problems such as PTSD. Basic counseling practices common to many treatment responses for PTSD include education about the condition and provision of safety and support. A number of psychotropic agents, including Selective Serotonin Reuptake Inhibitors (SSRIs), alpha adrenergic antagonists, anti-convulsants, mood stabilizers, anti-psychotics, beta blockers, benzodiazepines, glucocorticoids, monoamine-oxidase inhibitors (MAOIs), heterocyclic anti-depressants, tricyclic anti-depressants and atypical antidepressants have been proposed to be of use to treat PTSD. However, most of these agents treat a subset of symptoms of PTSD, and many are not particularly efficacious or have unwanted side-effects. A need remains for additional therapeutic strategies for treating PTSD.

SUMMARY

Methods are disclosed for treating post traumatic stress disorder (PTSD) in a subject. The methods include administering a therapeutically effective amount of a neurotoxin to a corrugator supercilii and/or a procerus muscle of the subject to cause paralysis of the corrugator supercilii and/or a procerus muscle, thereby treating the PTSD in the subject.

In some embodiments, the methods include selecting a subject with PTSD, and administering a therapeutically effective amount of Botulinum toxin A to a corrugator supercilii muscle and a procerus muscle of the subject, in order to cause paralysis of the corrugator supercilii muscle and procerus muscle and treat the PTSD in the subject. In some non-limiting examples, the subject does not have an underlying muscular physical condition. In other examples the Botulinum toxin A is selectively administered only to the corrugator supercilii muscle or procerus muscle or selectively only to both of these muscles.

The foregoing and other features and advantages will become more apparent from the following detailed description of several embodiments, which proceeds with reference to the accompanying figures.

BRIEF DESCRIPTION OF THE FIGURES

FIGS. 2A-2B show Botulinum toxin dose used to treat the frown in a typical woman (FIG. 2A) and man (FIG. 2B). The landmarks for the injection are as follows (see also Carruthers et al., Derm. Surg. 24:1189-1194, 1998). The injection of the procerus is below a line joining the medial end of both eyebrows. The landmark for the next injections is a line vertically above the inner canthus and the superior margin of the orbit. Botulinum toxin is injected just superior to the first injection point. Next an injection is made 1 centimeter (cm) medial and one-half cm superior to the second two injections line. The numbers refer to the number of BTX Units injected in the area shown.

DETAILED DESCRIPTION

Methods are disclosed herein for treating post-traumatic stress disorder (PTSD). The methods include administering a therapeutically effective amount of a neurotoxin to the corrugator supercilii and/or the procerus muscle of the subject to cause paralysis, thereby treating the PTSD in the subject. In specific non-limiting examples, the neurotoxin is Botulinum toxin A.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Absent an underlying physical disorder: A phrase used to describe a muscular disorder (for example, torticollis) or cosmetic issue (for example, wrinkles) that is already known to be reduced or prevented by treatment with botulinum toxin that is not present in a subject. For example, the method includes selecting a subject that does not have a muscular disorder or condition, such as a subject that does not have spasms, cramping, tightness of muscles caused by medical problems, or torticollis. A physical condition can be someone that has need and/or interest in cosmetic application of Botulinum toxin, such as to decrease wrinkles. For example, the method includes selecting a subject that does not have an underlying cosmetic issue (such as wrinkles) and/or is not selected for treatment for this underlying cosmetic disorder.

Ameliorating or ameliorate: Any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation. For example, a clinical guide to monitor the effective amelioration of a psychiatric disorder, such as depression, is found in the Structured Clinical Interview for DSM-IV Axis I mood disorders ("SCID-P") (see fourth edition of *Diagnostic and Statistical Manual of Mental Disorders* (1994) Task Force on DSM-IV, American Psychiatric Association ("DSM-IV"); Kaplan, Ed. (1995); *Comprehensive Textbook of Psychiatry/VI*, vol. 1, sixth ed., pp. 621-627, Williams & Wilkins, Baltimore, Md.).

Administration: To provide or give a subject an agent by any effective route. Exemplary routes of administration include, but are not limited to, oral; injection, continuous or intermittent infusion (such as subcutaneous, intramuscular, intradermal, intrathecal, epidural, intracranial, intraperitoneal, and intravenous); sublingual; rectal; transdermal; intranasal; vaginal; and inhalation routes.

Anti-Depressant Medications: A pharmaceutical agent that is administered as a treatment for depression. Antidepressant medications include synthesized chemical compounds as well as naturally occurring or herbal remedies such as St. John's Wort. Generally, these medications are administered orally, but they may also be administered in any form of use to a medical practitioner. Examples of antidepressant medications include tricyclic antidepressants, which generally affect the two chemical neurotransmitters, norepinephrine and serotonin. Tricyclics include imipramine, amitriptyline, nortriptyline, and desipramine Monoamine oxidase inhibitors (MAOIs) are also used as antidepressants. MAOIs approved for the treatment of depression include phenelzine (NARDIL®), tranylcypromine (PARNATE®), and isocarboxazid (MARPLAN®). Medications that primarily affect the neurotransmitter serotonin, termed selective serotonin reuptake inhibitors (SSRIs), are also used as antidepressants. These include escitalopram HBr (LEXAPRO®), fluoxetine (PROZAC®), sertraline (ZOLOFT®Zoloft), fluvoxamine (LUVOX®), paroxetine (PAXIL®), and citalopram (CELEXA®). Additional medication of use affect both norepinephrine and serotonin, for example venlafaxine (EFFEXOR®) and nefazadone (SERZONE®), or agents such as phenelzine (NARDIL®Nardil), tranylcypromine (PARNATE®), mirtazepine (REMERON®), nefazodone (SERZONE®), triazolopyridine (trazodone), and bupropion (WELLBUTRIN®).

Anxiety disorder: Any disorder characterized by increased anxiety. Some common anxiety disorders are social phobia, post-traumatic stress disorder, panic disorder, panic attacks, and obsessive-compulsive disorder. Anxiety disorders can be accompanied by perceptual disturbances. Anxiety disorders can be caused by a medical disorder (e.g., endocrine disorders, lupus), medication side-effect (e.g., interferon), substance use disorder, neuroloic disorder (e.g., seizure disorder, brain injury), or have no clear cause.

Depressive Disorder: A mood disorder characterized by a predominantly sad or depressed mood, typically but not always of two or more weeks' duration. A depressive disorder also has other signs or symptoms accompanying a sad or depressed mood, including one or more of: decreased energy, appetite changes, weight gain or loss, insomnia or hypersomnia, recurrent thoughts of death, thoughts of suicide, loss of interest in usual activities, slowed thinking or cognitive speed, increased speech latency, decreased volume of speech, excessive or inappropriate guilt, diminished concentration, feeling sluggish, and slower than normal motor activity (such as gross motor, fine motor, speech). Depressive disorders can be accompanied by perceptual disturbances. Depressive disorders can be caused by a medical disorder (e.g., endocrine disorders, lupus), medication side-effect (e.g., interferon), substance use disorder, neurologic disorder (e.g., seizure disorder, traumatic brain injury), or have no clear cause.

Botulinum toxin: A toxin produced by the bacterium *Clostridium botulinum*, but which may either be obtained from a natural source or made by synthetic means. Seven immunologically distinct Botulinum neurotoxins have been characterized, these being respectively Botulinum neurotoxin serotypes A, B, $C_1$, D, E, F and G, each of which is distinguished by neutralization with type-specific antibodies. The different serotypes of Botulinum toxin vary in the animal species that they affect and in the severity and duration of the paralysis they evoke. For example, it has been determined that Botulinum toxin type A is 500 times more potent, as measured by the rate of paralysis produced in the rat, than is Botulinum toxin type B. Additionally, Botulinum toxin type B has been determined to be non-toxic in primates at a dose of 480 U/kg which is about 12 times the primate $LD_{50}$ for Botulinum toxin type A (Moyer et al., "Botulinum Toxin Type B: Experimental and Clinical Experience," in *Therapy With Botulinum Toxin*, Marcel Dekker, Inc. Jankovic et al. (eds.), pp. 71-85, 1994).

Depression: A mental state of depressed mood characterized by feelings of sadness, despair and discouragement. Depression includes feelings of sadness considered to be normal (mild depression), dysthymia, and major depression. Depression can resemble the grief and mourning that follows bereavement, and there are often feelings of low self esteem, guilt and self reproach, withdrawal from interpersonal contact and somatic symptoms such as alterations in eating habits and sleep disturbances.

Frown: To furrow the brow to show unhappiness or displeasure. This action uses the orbicularis oculi, the *frontalis* muscle and/or the corrugator supercilii muscle. This action can also include the use of the procerus muscle.

Hallucination: Altered, misperceived, or incorrect sensory experiences. See "perceptual disturbances" below for additional information.

Mood: A person's subjective report on their emotional perspective on self, situation, future, or past. While mood can fluctuate from states such as "happy," "sad," "angry," or "pleased" within a day, a prolonged state of sad or depressed mood is a defining characteristic of a depressive illness.

Mood disorder: A medical, neurologic, or psychiatric disorder with the primary sign or symptom as an alteration in mood. Mood disorders are usually classified as depressive (e.g., principal mood symptom is a sustained sad or depressed mood) or manic (e.g., principal mood symptom is a sustained expansive, elevated, or irritable mood). Symptoms or signs beyond the mood state proper may be required to diagnose a mood disorder.

Nightmare: A frightening dream that causes the interruption of sleep. Repeated instances of nightmares can lead to a specific sleep disorder diagnosis of Nightmare Disorder. Nightmares are also commonly observed as a symptom in PTSD and other anxiety conditions.

Perceptual disturbance: An altered perception or conscious experience of sensory information. A common perceptual disturbance is a hallucination (incorrect perception of auditory, visual, tactile, olfactory, or gustatory sense information). Another common perceptual disturbance is a flashback (the sensory experience of being in a different place and/or time, often in response to a sensory trigger (e.g., after hearing a car backfire, a combat veteran has a momentary sensation of being back at war)). Altered reality testing is sometimes used to describe a person experiencing perceptual disturbances because the person is not accurately perceiving sensory stimuli.

Post-Traumatic Stress Syndrome (PTSD): A disorder that can occur after experiencing a traumatic event that leaves a subject feeling scared, confused, and/or angry to the extent that daily activities are difficult to perform. A traumatic event can include combat or military exposure, child sexual or physical abuse, terrorist attacks, sexual or physical assault, serious accidents, and natural disasters (such as a fire, tornado, hurricane, flood, or earthquake). PTSD is defined by the Diagnostic and Statistical Manual (DSM), Fourth-Edition, Text Revision, published by the American Psychiatric Associating (DSM-IV-TR), and the DSM-V.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. In addition to biologically-neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

Psychiatric disorder: Any disorder that results in altered or abnormal behavior, function, or subjective distress in one or more of the following intrapersonal or interpersonal realms: mood, anxiety, memory, cognition, consciousness, perception, sexual experience, sleep, substance use/addiction, personality, attention/concentration, psychosis, identity, eating, or bodily function or integrity. A psychiatric disorder typically causes the patient or others around the patient noticing social, interpersonal, and/or occupational distress or dysfunction. The cause (etiology) of a psychiatric disorder may be idiopathic (unknown), or it may be due to a recognized psychosocial stressor, a medical disorder, or a neurological disorder.

Psychotic: A psychiatric condition in its broadest sense, as defined in the DSM-IV (Kaplan, ed. (1995) supra). Different disorders which have a psychotic component comprise different aspects of this definition of "psychotic." For example, in schizophreniform disorder, schizoaffective disorder and brief psychotic disorder, the term "psychotic" refers to delusions, any prominent hallucinations, disorganized speech, or disorganized or catatonic behavior. In psychotic disorder due to a general medical condition and in substance-induced psychotic disorder, "psychotic" refers to delusions or only those hallucinations that are not accompanied by insight. Finally, in delusional disorder and shared psychotic disorder, "psychotic" is equivalent to "delusional" (see DSM-IV, supra, page 273).

Objective tests can be used to determine whether an individual is psychotic and to measure and assess the success of a particular treatment schedule or regimen. For example, measuring changes in cognitive ability aids in the diagnosis and treatment assessment of the psychotic patient. Any test known in the art can be used, such as the so-called "Wallach Test," which assesses recognition memory (see below, Wallach, *J. Gerontol.* 35:371-375, 1980). Another example of an objective text that can be used to determine whether an individual is psychotic and to measure efficacy of an anti-psychotic treatment is the Stroop Color and Word Test ("Stroop Test") (see Golden, C. J., Cat. No. 30150M, in *A Manual for Clinical and Experimental Uses*, Stoelting, Wood Dale, Ill.). The Stroop Test is an objective neuropsychiatric test that can differentiate between individuals with psychosis and those without.

Psychosis: A psychiatric symptom, condition or syndrome in its broadest sense, as defined in the DSM-IV (Kaplan, ed. (1995) supra), comprising a "psychotic" component, as broadly defined above. Psychosis is typically defined as a mental disorder or condition causing gross distortion or disorganization of a person's mental capacity, affective response, and capacity to recognize reality, communicate, and relate to others to the degree of interfering with his capacity to cope with the ordinary demands of everyday life.

Psychotic major depression: A condition also referred to as psychotic depression (Schatzberg, *Am. J. Psychiatry* 149:733-745, 1992), "psychotic (delusional) depression," "delusional depression," and "major depression with psychotic features" (see the DSM-III-R). This condition is a distinct psychiatric disorder that includes both depressive and psychotic features. Individuals manifesting both depression and psychosis, i.e. psychotic depression, are often referred to as "psychotic depressives."

Seizure Disorder: A "paroxysmal event due to abnormal, excessive, hypersynchronous discharges from an aggregate of central nervous system (CNS) neurons" that may or may not result in observable changes in behavior (Chapter 363 of *Harrison's Principles of Internal Medicine* (Fauci A S, Kasper D L, et al. (editors), 17th Edition, 2008). A seizure is a single event while epilepsy or seizure disorder is a medical diagnosis to describe a condition characterized by repeated seizures. Various types of seizures include simple partial, complex partial, partial with secondary generalization, absence, atypical absence, generalized tonic-clonic, atonic, myoclonic, or unclassified. Brain injury as defined above is a recognized cause of seizures. Seizures can be associated with various additional clinical problems: cognitive changes, mood or anxiety changes, interictal behavior changes, sudden death, psychosocial impairments, occupational problems, or psychosis.

Scowl: A facial expression showing displeasure. Scowling primarily utilizes the corrugator supercilii muscle and the procerus muscle.

Selective Serotonin Reuptake Inhibitor (SSRI): A type of antidepressant medication that is prescribed for the treatment of various psychiatric conditions, including, but not limited to, a depressive disorder or an anxiety disorder. Commonly prescribed SSRIs include fluoxetine, paroxetine, sertraline, citalopram, escitalopram, and fluvoxamine Other non-limiting examples of SSRI include prodrug or pharmacologically active metabolite of these SSRI medications.

Sertraline: A selective serotonin reuptake inhibitor that is prescribed to treat one or more of the following indications: major depression or a depressive disorder, OCD, PTSD, panic disorder, social phobia, PMDD, or an anxiety disorder.

Sign: An observation, result, finding, or outcome on a medical test or examination that may indicate the presence of an associated medical, neurologic, or psychiatric condition. Non-limiting examples include observed behavior reported by a non-medical observer (e g, family member, friend, law enforcement officer, clergy, fellow member of a military unit); observed behaviors during clinical evaluation such as anxiety noted on mental status examination; psychological or neuropsychological test results; laboratory value from blood, urine, cerebrospinal fluid; radiologic examinations such as x-rays, CT or MR scans; physical examination results such as impaired coordination or disconjugate eye movements on neurological examination, or elevated blood pressure on physical examination; or oculomotor function on vestibulo-oculomotor examination.

Sleep disorder: A disorder of sleep that includes, but is not limited to, insomnia, disorders of daytime somnolence, parasomnias, chronobiological disorders, and sleep consequences of neurological disorders. Non-limiting examples of sleep disorders include rapid eye movement behavior disorder, restless legs syndrome, periodic leg movements of sleep, obstructive sleep apnea, central sleep apnea, nightmares, sleep terrors, sleepwalking, confusional arousals, sleep paralysis, sleep eating disorder, or narcolepsy (See, for example, CG Goetz (editor), *Textbook of Clinical Neurology*, $3^{rd}$ Edition, 2007, Chapter 54)

Sleep disturbance: An observed or reported alteration in the initiation, maintenance, or quality of sleep that may be a symptom or sign of a medical, neurological, or psychiatric disorder. A sleep disturbance also may be a symptom or sign of a sleep disorder.

Sleep Terrors: An awakening from sleep characterized by intense anxiety upon awakening. Sleep terrors can be differentiated from nightmares because there is significantly less recall of frightening dream content in sleep terrors. Sleep terrors may be present as a sign or symptom of another psychiatric disorder. Sleep terrors can be difficult to distinguish from nocturnal panic attacks.

Subject: Any mammal. In one embodiment, a subject is a human subject.

Symptom: A problem, complaint, or issue reported by a subject that is primarily a subjective complaint. Pain, fatigue, or changes in mood are commonly reported symptoms. Symptoms are distinguished from signs in that signs typically can be confirmed with objective evidence such as observation, tests or examinations, whereas symptoms rely upon the subject's self-report.

Therapeutically effective amount: A quantity of treatment, such as drug, for example a neurotoxin such as Botulinum toxin A, sufficient to achieve a desired effect in a subject being treated. For instance, this can be the amount of Botulinum toxin A necessary to impair contraction of, or paralyze, a facial muscle. This can also be the amount of a therapy, such as light therapy or psychotherapy, sufficient to relieve a symptom of a disorder, such as depression. This can also be the amount of an antidepressant sufficient to alter the mood of a subject.

Unit equivalents: An amount of Botulinum Toxin (BTX) that is equivalent to standard Units of Botulinum Toxin A (BTX-A). A standard Unit of BTX-A is defined as the mean $LD_{50}$ for female Swiss Webster mice weighing 18-20 grams (Schantz and Kaultner, *J. Assoc. Anal. Chem.* 61: 96-99, 1978). The estimated human $LD_{50}$ for a 70-kg person is 40 Units/kg or about 2500-3000 Units.

BOTOX™ (Botulinum toxin A, Allergan, Inc., Irvine, Calif., U.S.A.) is sold in 100 Unit vials. DYSPORT™ (Speywood Pharmaceuticals, Ltd., Maidenhead, U.K.) is sold in 300 or 500 Unit vials. For cosmetic uses, the vial contents are typically diluted with 1 or 2 ml of sterile saline solution, which for BOTOX™ provides a 100 or 50 Unit/ml dilution. DYSPORT™ BTX-A is roughly three fold less toxic than BOTOX™ and approximately three-fold greater amounts of the DYSPORT™ product will usually be injected to achieve the same result as would be obtained using a specific number of Units of BOTOX™.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Botulinum Toxin

Botulinum toxin (BTX), produced by the bacterium *Clostridium botulinum* reversibly paralyzes striated muscle when administered in sub-lethal doses. BTX has been used in the treatment in a number of neuromuscular disorders and conditions involving muscular spasm including, but not limited to, dystonia, hemifacial spasm, tremor, spasticity (e.g. resulting from multiple sclerosis), anal fissures and various ophthalmologic conditions (for example, see Carruthers et al., *J. Amer. Acad. Derm.* 34:788-797, 1996). A Botulinum toxin type A complex has been approved by the U.S. Food and Drug Administration for the treatment of blepharospasm, strabismus and hemifacial spasm.

BTX is a generic term covering a family of toxins produced by *C. botulinum* comprising up to eight serologically distinct forms (A, B, $C_1$, $C_2$, D, E, F and G). These toxins are among the most powerful neuroparalytic agents known (c.f. Melling et al., *Eye* 2:16-23, 1988). Serotypes A, B and F are the most potent. Without being bound by theory, the mode of action is believed to be an inhibition of the release of acetylcholine by the presynaptic nerve.

Botulinum toxin type A can be obtained by establishing and growing cultures of *Clostridium botulinum* in a fermenter and then harvesting and purifying the fermented mixture in accordance with known procedures. Alternatively, the Botulinum toxin serotypes are initially synthesized as inactive single chain proteins which must be cleaved or nicked by proteases to become neuroactive. High quality crystalline Botulinum toxin type A can be produced from the Hall A strain of *Clostridium botulinum*. The Schantz process can be used to obtain crystalline Botulinum toxin type A (see Schantz et al., *Microbiol Rev.* 56:80-99, 1992). Generally, the Botulinum toxin type A complex can be isolated and purified from an anaerobic fermentation by cultivating *Clostridium botulinum* type A in a suitable medium. This process can be used, upon separation out of the non-toxin proteins, to obtain pure Botulinum toxins, such as for example: purified Botulinum toxin type A with an approximately 150 kD molecular weight, purified Botulinum toxin type B with an approximately 156 kD molecular weight and purified Botulinum toxin type F with an approximately 155 kD molecular weight.

Botulinum toxins and/or Botulinum toxin complexes can be obtained from List Biological Laboratories, Inc., Campbell, Calif.; the Centre for Applied Microbiology and Research, Porton Down, U.K.; Wako, Osaka, Japan; Metabiologics, Madison, Wis.) as well as from Sigma Chemicals, St Louis, Mo.

The initial cosmetic use of BTX was for treatment of forehead frown lines as reported in Carruthers and Carruthers, *J. Dermatol. Surg. Oncol.* 18:17-21, 1992. The clinical effects of peripheral intramuscular Botulinum toxin type A are usually seen within one week of injection. The typical duration of symptomatic relief from a single intramuscular injection of Botulinum toxin type A averages about three months. BTX-A serotype is available commercially for pharmaceutical use under the trademarks BOTOX™ (Allergan, Inc., Irvine, Calif., U.S.A.) and DYSPORT™ (Speywood Pharmaceuticals, Ltd., Maidenhead, U. K.). BOTOX™ consists of a purified Botulinum toxin type A complex, albumin and sodium chloride packaged in sterile, vacuum-dried form. Specifically, each vial of BOTOX™ contains about 100 Units (U) of *Clostridium botulinum* toxin type A purified neurotoxin complex, 0.5 milligrams of human serum albumin and 0.9 milligrams of sodium chloride in a sterile, vacuum-dried form without a preservative.

The Botulinum toxin type A is made from a culture of the Hall strain of *Clostridium botulinum* grown in a medium containing N-Z amine and yeast extract. The Botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C.

BOTOX™ is sold in 100 Unit vials. DYSPORT™ is sold in 300 or 500 Unit vials. BTX-A is roughly three-fold less toxic than BOTOX™ and approximately three-fold greater amounts of the DYSPORT™ product will usually be injected to achieve the same result as would be obtained using a specific number of Units of BOTOX™.

For cosmetic uses, the vial contents are typically diluted with 1 or 2 ml of sterile saline solution, which for BOTOX™ provides a 100 or 50 Unit/ml dilution. (DYSPORT™ can also be utilized.) For example, BOTOX™ can be reconstituted with sterile, non-preserved saline prior to intramuscular injection. To reconstitute vacuum-dried BOTOX™, sterile normal saline without a preservative (0.9% Sodium Chloride Injection) is used by drawing up the proper amount of diluent in the appropriate size syringe. Since BOTOX™ may be denatured by bubbling or similar violent agitation, the diluent is gently injected into the vial. For sterility reasons BOTOX™ is preferably administered within four hours after the vial is removed from the freezer and reconstituted. During these four hours, reconstituted BOTOX™ can be stored in a refrigerator at about 2° C. to about 8° C. Reconstituted, refrigerated BOTOX™ has been reported to retain its potency for at least about two weeks (see Neurology, 48:249-53:1997).

Methods for Treatment of Post Traumatic Stress Disorder

Methods are provided herein for treating post traumatic stress disorder (PTSD) in a subject. The method includes administering a therapeutically effective amount of a neurotoxin to a facial muscle involved in frowning, scowling, or a sad appearance. The agent causes partial or complete paralysis of the facial muscle, thereby affecting the ability of the subject to frown and thereby treat PTSD. The injection sides for treatment include the procerus muscle and/or the corrugator supercilii muscle. In some embodiments a therapeutically effective amount of BTX, such as BTX A, is administered to the procerus muscle and the corrugator supercilii muscle. In some embodiments, BTX is not injected into the orbicularis oculi, frontalis, and/or the depressor anguli oris muscles (trianglaris muscle). In other embodiments, BTX is injected into the depressor anguli oris muscles (trianglaris muscle).

The method involves identifying or selecting subjects who have PTSD and administering the treatment to these subjects. The subject can be female or male. The Diagnostic and Statistical Manual (DSM), Fourth-Edition, Text Revision (DSM-IV-TR) classifies PTSD as a specific type of an anxiety disorder, characterized by aversive anxiety-related experiences, behaviors, and physiological responses that develop after exposure to a psychologically traumatic event (sometimes months after). The diagnostic criteria for PTSD include exposure to a traumatic event, persistent re-experiencing, persistent avoidance of emotional numbing, persistent symptoms of increased arousal, significant impairment and duration of symptoms for more than one month. PTSD results in clinically significant distress or impairment in social, occupational, or other important areas of functioning. The features persist for longer than 30 days, which distinguishes it from the briefer acute stress disorder or an anxiety disorder.

A subject can be selected that has PTSD as defined by the DSM-IV-TR criteria. A subject can also be selected that has PTSD as defined by the DSM-V criteria. A subject can be selected who has experienced trauma. The subject can be an adult or a child. The subject can be a military veteran.

In some embodiments, the subject has been exposed to a traumatic event in which both of the following have been present: (a) the subject experienced, witnessed, or was confronted with an event or events that involved actual or threatened death or serious injury, or a threat to the physical integrity of self or others (b) the subject's response involved intense fear, helplessness, or horror. Generally, for a subject with PTSD, the traumatic event is persistently re-experienced in one (or more) of the following ways for a period of over one month:

(1) recurrent and intrusive distressing recollections of the event, including images, thoughts, or perceptions;
(2) recurrent distressing dreams of the event;
(3) acting or feeling as if the traumatic event were recurring (includes a sense of reliving the experience, illusions, hallucinations, and dissociative flashback episodes, including those that occur upon awakening or when intoxicated);
(4) intense psychological distress at exposure to internal or external cues that symbolize or resemble an aspect of the traumatic event; and
(5) physiological reactivity on exposure to internal or external cues, that symbolize or resemble an aspect of the traumatic event or both.

The presently claimed methods can reduce the number of times that the traumatic event is re-experienced, or can reduce the intensity of the responses to internal or external cues that symbolize or represent the traumatic event.

A subject with PTSD generally has persistent avoidance of stimuli associated with the trauma and numbing of general responsiveness (not present before the trauma), as indicated by three (or more) of the following symptoms for over one month:

(1) efforts to avoid thoughts or conversations associated with the trauma;
(2) efforts to avoid activities, places, or people that arouse recollections of the trauma;
(3) inability to recall an important aspect of the trauma;
(4) markedly diminished interest or participation in significant activities;
(5) feeling of detachment or estrangement from others;
(6) restricted range of affect (e.g., unable to have loving feelings); and
(7) sense of a foreshortened future (e.g., does not expect to have a career, marriage, children, or a normal life span).

The presently claimed method can decrease one, two, three, four, five, six, or all seven of the symptoms.

A subject with PTSD also has persistent symptoms of increased arousal (not present before the trauma), as indicated by two (or more) of the following:

(1) difficulty falling or staying asleep;
(2) irritability or outbursts of anger;
(3) difficulty concentrating;
(4) hypervigilance; and
(5) exaggerated startle response.

The presently claimed methods can decrease one, two, three, four or all five of these persistent symptoms.

A subject is selected that has PTSD. In some embodiments, the subject does not have an underlying physical condition that is being treated by BTX, such as a musculoskeletal condition, such as torticollis, blepharospasm, or other disorder of muscular contractions. In other embodiments, the subject does not have a muscular disorder or condition. In some examples, the subject does not have spasms, cramping, and tightness of muscles cause by musculoskeletal conditions/disease. In additional embodiments, the subject has (or does not have) wrinkles, and is not being treated using Botulinum toxin for any cosmetic purposes, including the treatment of wrinkles. In some embodiments, the subject has a comorbid condition.

In additional embodiments, the subject does not have an anxiety disorder other than PTSD. Thus, the subject does not have an acute stress disorder or an anxiety disorder. In further embodiments, the subject does not have depression, such as major depression or a mood disorder. Thus, in some embodiments, PTSD is the sole psychological disorder; the subject does not have, for example schizophrenia, depression, other anxiety disorders, and/or obsessive compulsive disorder. In some embodiments, the subject does not have a psychotic disorder. In additional embodiments, the subject does not have a sleep disorder, sleep terrors or a sleep disturbance cause by any factor other than PTSD.

In additional embodiments, the methods disclosed herein are utilized concurrently with cognitive behavioral therapy and/or psychotherapy. In additional embodiments, BTX, such as BTX A, is administered in conjunction with other agents, such as propranolol or cortisol.

The modality can be the administration of a therapeutically effective amount of an antidepressant used for the treatment of PTSD. In particular examples, the additional modality is the administration of a therapeutically effective amount of an antidepressant medication, such as a tricyclic antidepressant or a selective serotonin reuptake inhibitor (SSRI), or other classes of drugs (such as an MAOI or a tricyclic antidepressant).

In other embodiments, the subject is administered additional anti-depressant medication, including, but not limited to SSRIs, such as citalopram, escitalopram, fluoxetine, fluvoxamine, paroxetine, and sertraline, and/or MAOIs. In further embodiments, Botulinum toxin is administered in conjunction with an alpha-adrenergic antagonist, such as clonidine, an anti-convulsant or mood stabilizers (for example, carbamazepine (TERGRETOL®), Topiramate (TOPAMAX®), Zolpidem (AMBIEN®), Lamotrigine (LAMICTAL®), Valproic acid (DEPAKENE®), lithium carbonate, buspirone (BUSPAR®), and alpha adrenergic blockers such as Prazosin (MINIPRESS®)). In additional embodiments, Botulinum toxin is administered with an antipsycholic agent, such as risperidone, or an atypical antidepressant, a beta blocker (such as propanolol), a benzodiazepine, a glucocorticoid (such as cortiosterone), a heterocyclic antidepressant, such as amitriptyline, or imipramine, or a MAOI, such as phenelzine.

The BTX, such as BTX A, can be administered simultaneously or sequentially with the additional modality of treatment. In one embodiment, a therapeutically effective amount of BTX, such as BTX A, is administered in combination with at least one additional modality of treatment for PTSD. Useful modalities are listed above. The modality of treatment can also be physical, such as electroconvulsive therapy, light therapy, or electromagnetic radiation. The modality can also be psychotherapy, exercise or meditation. A single modality of treatment can be combined with the BTX treatment, or a combination of additional modalities can be used with the BTX treatment. Thus, in one example, a subject taking a therapeutically effective amount of an antidepressant medication (such as an SSRI), or undergoing a therapeutic protocol, can be treated with BTX, such as BTX A, during the course of the additional treatment. The subject can be administered an additional therapeutic agent, such as a therapeutically effective amount of one or more of: a Selective Serotonin Reuptake Inhibitor (SSRI), an alpha adrenergic antagonist, an anti-convulsant, a mood stabilizer, an anti-psychotic agent, a beta blocker, a benzodiazepine, a glucocorticoid, a monamine-oxidase inhibitor (MAOIs), a heterocyclic anti-depressant, a tricyclic anti-depressant and/or an atypical anti-depressant. In one specific example, BTX is administered to a subject in conjunction with a therapeutically effective amount of beta blocker, such as propanolol.

BTX, such as BTX A, can be administered after the treatment with the additional agent has been terminated, or prior to the initiation of therapy, such as the administration of the antidepressant medication, psychotherapy, or a physical treatment protocol. Thus, the treatment can be simultaneous. In other embodiments, BTX is administered in the absence of treatment with these agents.

Without being bound by theory, decreased movement of muscles that a neural circuit that is involved in PTSD lessen the symptoms of anxiety PTSD ensues. Denervation of the frown muscles results in a decreased ability of the treated subject to frown, and thus inhibits fear, anger and sadness, contributing to a subjective sense of less anxiety and/or preventing triggering of the memory. Improvement can be objectively assessed by the DSM-IV or DMSV-V criteria, or by standardized tests known in the art. As noted above, PTSD can be assessed, for example, by the Beck Depression Inventory II (1996, Harcourt). A very straightforward test is to ask the subject to report whether the intensity of the symptoms. For example the present methods can result in (1) decreased efforts to avoid thoughts, feelings, or conversations associated with the trauma; (2) decreased efforts to avoid activities, places, or people that arouse recollections of the trauma; (3) increased recall of aspect of the trauma (memory); (4) increased interest or participation in significant activities; (5) fewer feelings of detachment or estrangement from others; (6) an increased range of affect (e.g., able to show loving feelings); (7) better sense of the future (e.g., more positive outlook with regard to a career, marriage, children, or a normal life span); and/or (8) decreased distress in relation to recall of traumatic events. The presently claimed methods can achieve one, two, three, four, five, six, seven or all eight of the results.

The present methods can also result in a decrease in symptoms of PTSD. In some embodiments, the subject has (1) less difficulty falling or staying asleep; (2) less irritability or outbursts of anger; (3) less difficulty concentrating; (4) less hypervigilance; and/or a (5) less exaggerated startle response. The methods can decrease one, two, three, four or all five of these symptoms. The presently claimed methods can also decrease nightmares or night terrors in the subject.

The treatment can be repeated when the partial or complete muscle paralysis induced by the agent begins to abate. Alternatively, one can also wait for any signs or symptoms of PTSD to also recur after the muscular activity returns.

An exemplary injection technique involves the use of a short, narrow needle (e.g. ½ inch or 8 mm; 30-gauge) with an insulin- or tuberculin-type syringe. Subjects are typically treated in the seated position. The skin area is cleaned with an alcohol swab. A single syringe may be used for multiple injections to treat different locations in a single muscle or more than one muscle. Typically, the plunger of the syringe is depressed as the needle is withdrawn so that toxin is evenly distributed at the injection site. Pressure or gentle massage may be applied at the injection site to assist in dissipating the toxin. The toxin will typically migrate approximately 1 cm from the site of injection. Without being bound by theory, the toxin (such as BTX A) does not cross the blood brain barrier.

Electromyographic (EMG) guided needles may be used for injection to determine needle location of a high degree of accuracy, although this technique is generally not necessary.

For applications of BTX, such as BTX A, total dose per treatment can be varied and depends upon the condition being treated and the site of application of BTX. For example, a total dose of about 10 to about 60 Units, such as about 20 to about 50 Unity equivalents, about 30 to about 60 Units, about 29 to about 40 units, or about 20 to about 40 Unit equivalents. The BTX, such as BTX A will typically be applied to corrugator supercilii and the procerus muscle (see, Carruthers and Carruthers, Dermatol. Surg. 24:1168-1170, 1998 for dosing information). In some embodiments, BTX, such as BTX A, is not administered to the orbicularis oculi, frontalis, and/or the depressor anguli oris muscles (trianglaris muscle). In one specific non-limiting example, about 20 to about 50 Unit equivalents of BTX A is administered only to the corrugator supercilii and/or the procerus muscle or both. In further embodiments, a total dose of about 20 to about 60 Unit equivalent of BTX are administered to the corrugator supercilii, procerus muscle and the depressor angularis oris muscle.

In some non-limiting examples, a total of about 28 to about 58 Unit equivalants of BTX are administered to the corrugator supercilii, procerus muscle, and depressor angularis oris muscles, wherein about 4 Unit equivalents are administered to the left depressor angularis oris muscle and to the right depressor angularis oris muscle.

Onset of muscle paralysis following injection usually occurs within days of treatment, although it can take up to ten days for full paralysis to occur. In some embodiments, it can take one or two days for relief of symptoms, but it may take longer, such as a week or two weeks for improvement. The duration of paralysis will vary from patient to patient. Typically, duration will be from two to eight months, for example about three to about six months, or for example about three months, before subsequent treatment is required to alleviate the condition, although BTX can have an efficacy for up to 12 months (Naumann et al., *European J. Neurology* 6 (Supp 4): S111-S115, 1999).

Administration of the BTX repeated. In some embodiments, the BTX can be repeated at about two to about six month intervals, such as at about two, three, four, five, six, seven or eight month intervals. In other embodiments, administration is provided over a period of about about six months, or for about one, about two, about three, about four or about five years. Thus, in some non-limiting examples, BTX is administered every two to eight months for a period of one, two, three, four or five years.

Thus, in one specific, non-limiting example, to treat PTSD, the corrugator supercilii and/or the procerus muscle is treated repeatedly. For example, about 30 to about 60 Unit equivalents of BTX A, such as about 20 to about 40 Unit equivalents, or about 30 to about 40 Unit equivalents of BTX A, is administered to the corrugator supercilii and/or the procerus muscle. After a period of about three months, and additional about 30 to about 60 Unit equivalents, such as about 20 to about 40 Unit equivalents, or about 30 to about 40 Unit equivalents, of BTX A is administered to the corrugator supercilii and/or procerus muscle. This treatment can be administered as many times as needed to alleviate PTSD. Another neurotoxin can be used similarly, such as another BTX.

Figure 1:
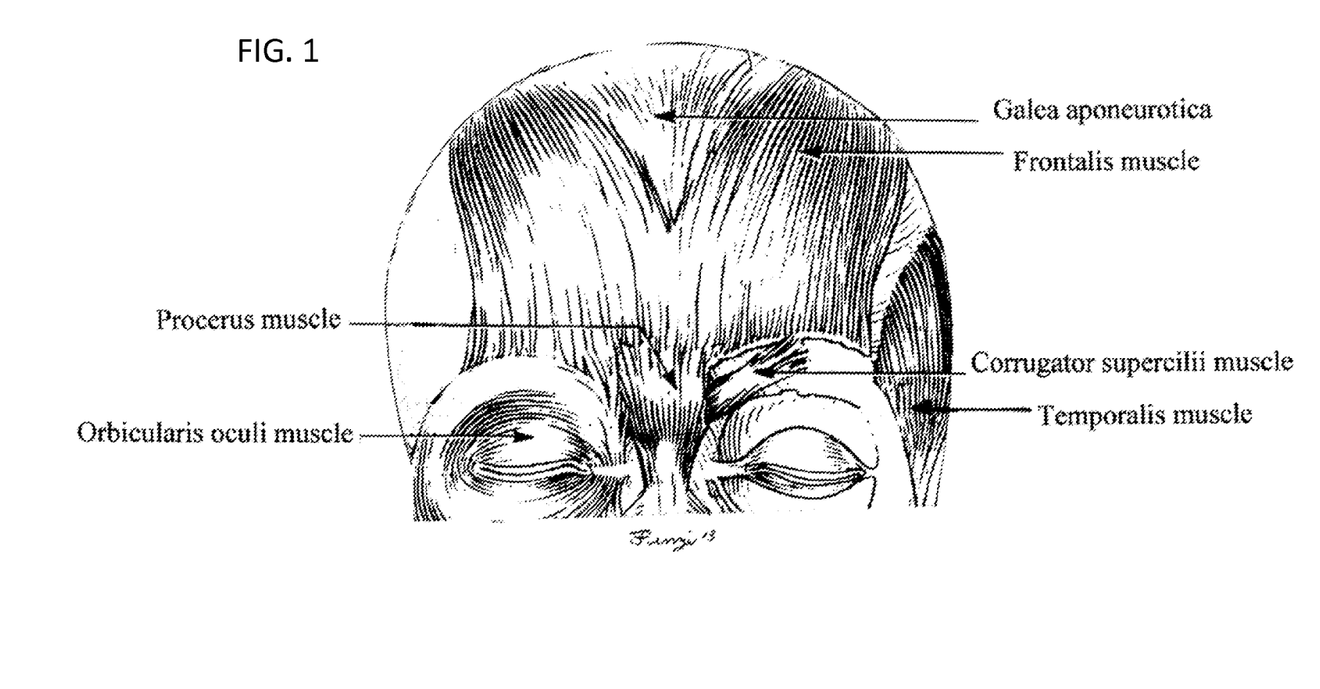
FIG. 1 is a schematic diagram of a frontal view of the musculature of the human face and neck. Injection sites for a neurotoxin, such as Botullinum Toxin (BTX) including the procerus and the corrugator supercilii are shown.
Figure 2A:
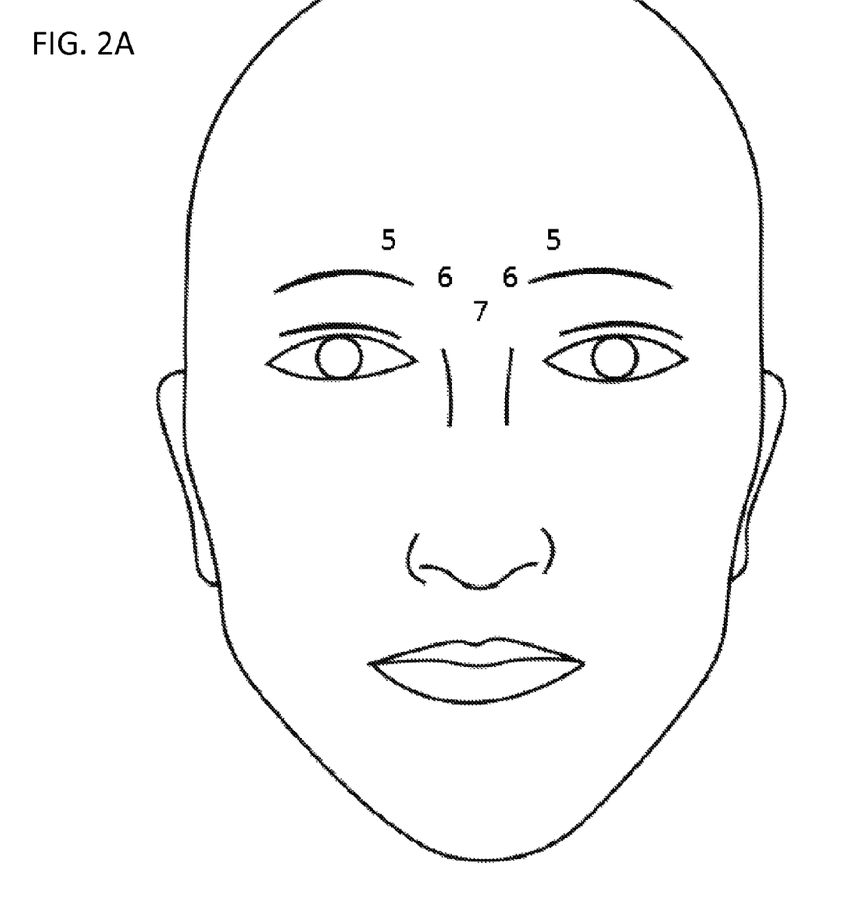
Figure 2B:
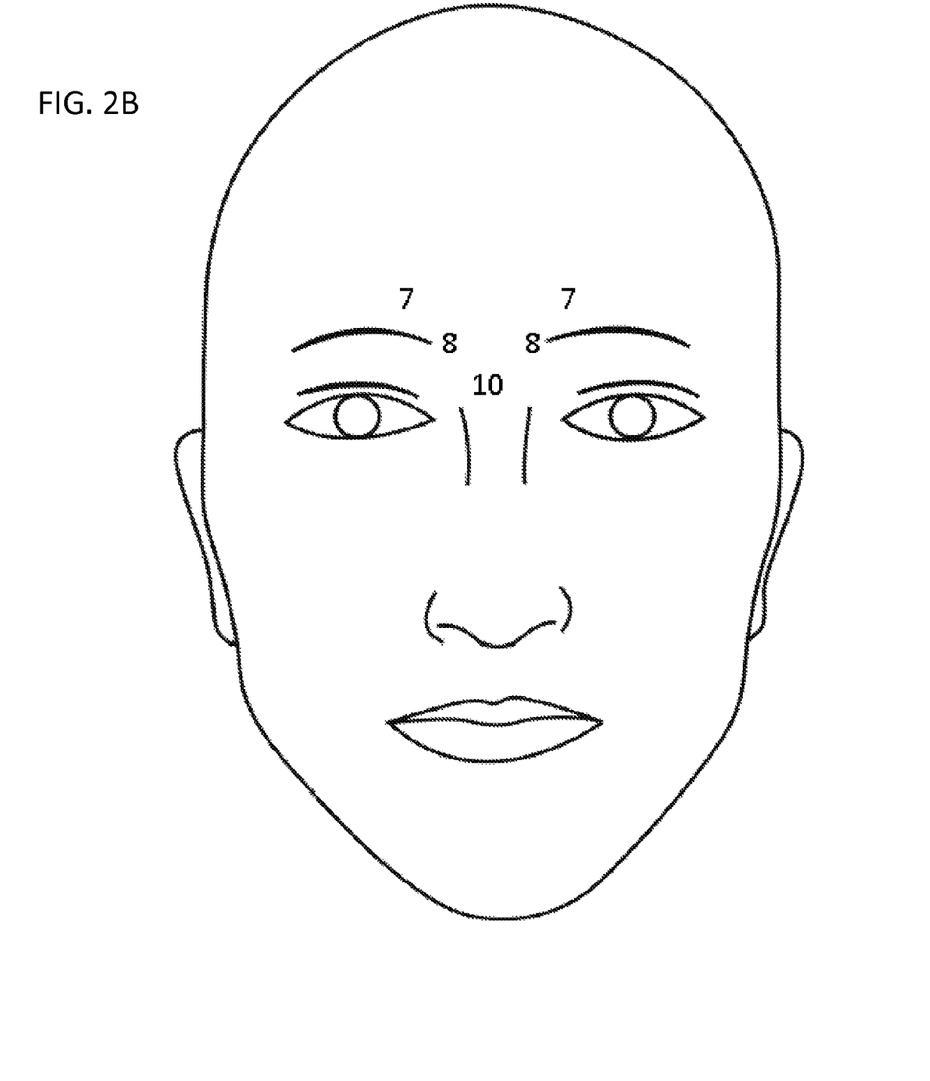

FIGS. 2A-2B show Botulinum toxin dose used to treat the frown in a typical woman (FIG. 2A) and man (FIG. 2B). The landmarks for the injection are as follows (see also Carruthers et al., *Derm. Surg.* 24:1189-1194, 1998). The injection of the procerus is below a line joining the medial end of both eyebrows. The landmark for the next injections is a line vertically above the inner canthus and the superior margin of the orbit. Botulinum toxin is injected just superior to the first injection point. Next an injection is made 1 centimeter (cm) medial and one-half cm superior to the second two injections. The numbers refer to the number of BTX Units injected in the area shown.

The disclosure is illustrated by the following non-limiting Examples.

EXAMPLES

The following example document treatment of PTSD by administering a neurotoxin to a corrugator supercilii and/or a procerus muscle of the subject.

Example 1

Case Study

A woman presented who had been married to a veteran from special forces. The veteran threatened to kill her every day if she left him. The woman eventually managed to leave her husband. She was diagnosed as suffering from PTSD by many therapists; the first diagnosis of PTSD was in 1990.

The subject experienced symptoms of PTSD, such as avoidance of situations where she felt symptoms would be triggered. She reacted strongly when people shouted at her, and often had an anger response to specific triggers. She tried many treatments for PTSD without success. She then consulted a plastic surgeon.

She had BOTOX® treatment in her frown lines repeated three times before the lines responded fully. After the third treatment, she reported no longer feeling angry. The beneficial effects of the BOTOX®, specifically a reduction in her anger lasted for 3 months. Repeat treatments resulted in a specific decrease in her response to triggers, and a decrease in anger.

It will be apparent that the precise details of the methods or compositions described may be varied or modified without departing from the spirit of the described invention. We claim all such modifications and variations that fall within the scope and spirit of the claims below.

The invention claimed is:

1. A method for treating post traumatic stress disorder (PTSD) in a human subject, comprising administering a therapeutically effective amount of a Botulinum toxin to a corrugator supercilii and a procerus muscle of the human subject to cause paralysis of the corrugator supercilii and the procerus muscle, thereby treating the PTSD in the human subject.

2. The method of claim 1, wherein the human subject does not have any other psychiatric disorder.

3. The method of claim 1, wherein the human subject does not have a muscular disorder.

4. The method of claim 1, wherein the Botulinum toxin is Botulinum toxin A.

5. The method of claim 4, wherein about 20-50 Unit equivalents of Botulinum toxin type A are administered to the corrugator supercilii and the procerus muscle in the human subject.

6. The method of claim 5, further comprising administering an additional dose of about 20-50 Unit equivalents of Botulinum toxin type A to the corrugator supercilii and the procerus muscle after about two to six months.

7. The method of claim 1, wherein the human subject is female.

8. The method of claim 1, further comprising administering electroconvulsive therapy, light therapy, or electromagnetic radiation to the human subject.

9. The method of claim 1, wherein the PTSD was caused by combat exposure, child abuse, a terrorist attack, assault, an accident, or a natural disaster.

10. A method for treating PTSD in a human subject, comprising administering a therapeutically effective amount of a Botulinum toxin to facial muscles of the human subject, wherein the facial muscles consist of a corrugator supercilii and a procerus muscle, thereby paralyzing the corrugator supercilii and the procerus muscle and treating the PTSD in the human subject.

11. A method for treating post traumatic stress disorder (PTSD) in a human subject, comprising
    selecting a human subject with PTSD, and
    administering a therapeutically effective amount of about 20 to about 40 Unit equivalents of Botulinum toxin A to a corrugator supercilii muscle and a procerus muscle of the human subject to cause paralysis of the corrugator supercilii muscle and procerus muscle,
    thereby treating the PTSD in the subject, wherein the human subject does not have an underlying muscular physical condition.

12. The method of claim 11, wherein about 29 to about 40 Unit equivalents of Botulinum toxin type A are administered to the corrugator supercilii muscle and the procerus muscle of the human subject.

13. The method of claim 11, further comprising administering an additional dose of about 30-60 Unit equivalents of Botulinum toxin type A to the corrugator supercilii muscle and the procerus muscle after about two to six months.

14. The method of claim 11, further comprising administering to the human subject a therapeutically effective amount of an additional modality of treatment.

15. The method of claim 14, wherein the additional modality of treatment comprises administration of an anti-depressant, psychotherapy, a beta blocker, or behavioral therapy.

16. The method of claim 14, wherein the additional modality of treatment comprises Selective Serotonin Reuptake Inhibitor (SSRI), an alpha adrenergic antagonist, an anti-convulsant, a mood stabilizer, an anti-psychotic, a beta blocker, a bezodiazepine, a glucocorticoid, monoamine-oxidase inhibitor (MAOIs), a heterocyclic anti-depressant, or a tricyclic anti-depressant.

17. The method of claim 11, further comprising performing a psychological assessment on the human subject.

18. The method of claim 17, wherein the human subject reports one or more of: (1) decreased efforts to avoid thoughts, feelings, or conversations associated with the trauma; (2) decreased efforts to avoid activities, places, or people that arouse recollections of the trauma; (3) increased recall of aspect of the trauma (memory); (4) increased interest or participation in significant activities; (5) fewer feelings of detachment or estrangement from others; (6) an increased range of affect (e.g., able to show loving feelings); and (7) a better sense of the future, following the administration of Botulinum toxin A.

19. The method of claim 17, wherein the human subject reports one or more of (1) less difficulty falling or staying asleep; (2) less irritability or outbursts of anger; (3) less difficulty concentrating; (4) less hypervigilance; and (5) a less exaggerated startle response, following the administration of Botulinum toxin A.

20. The method of claim 11, wherein the human subject is a female.

* * * * *